US00PP30411P2

(12) United States Plant Patent
Heuger

(10) Patent No.: US PP30,411 P2
(45) Date of Patent: Apr. 16, 2019

(54) ***HELLEBORUS* PLANT NAMED 'COSEH 3130'**

(50) Latin Name: ***Helleborus niger* X *Helleborus* x *hybridus***
Varietal Denomination: COSEH 3130

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 15/732,550

(22) Filed: Nov. 27, 2017

(51) Int. Cl.
*A01H 5/02* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 3130', characterized by its relatively compact, upright and mounding plant habit; moderately vigorous growth habit; dark green-colored leaves; freely flowering habit; single white-colored flowers proximally with dense greyed purple-colored spots; and good garden performance.

2 Drawing Sheets

Botanical designation: *Helleborus niger* X *Helleborus* x *hybridus*.

Cultivar denomination: 'COSEH 3130'.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 3130'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in 2010 of a unnamed selection of *Helleborus niger*, not patented, as the female, or seed parent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in 2012.

Asexual reproduction of the new *Helleborus* plant by divisions in a controlled environment in Glandorf, Germany since 2013 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3130'. These characteristics in combination distinguish 'COSEH 3130' as a new and distinct *Helleborus* plant:

1. Relatively compact, upright and mounding plant habit.
2. Moderately vigorous growth habit.
3. Dark green-colored leaves.
4. Freely flowering habit.
5. Single white-colored flowers proximally with dense greyed purple-colored spots.
6. Good garden performance.

Plants of the new *Helleborus* and the parent selections differ primarily in flower color as plants of the female parent selection have flowers that are solid white in color and plants of the male parent selection have flowers that are white with darker-colored spots.

Plants of the new *Helleborus* can be compared to plants of *Helleborus orientalis* 'HLR 160', disclosed in U.S. Plant Pat. No. 21,504. In side-by-side comparisons, plants of the new *Helleborus* differ primarily from plants of 'HLR 160' in flower color as plants of 'HLR 160' have flowers with denser greyed purple-colored spots present on a larger area of the sepals. In addition, plants of 'HLR 160' do not "pink" under low temperature conditions whereas plants of 'COSEH 3130' will "pink" under low temperature conditions.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 3130' grown in a container.

The photograph on the second sheet is a close-up view of typical flowers and flower buds of 'COSEH 3130'.

DETAILED BOTANICAL DESCRIPTION

The aforementioned photographs and following observations, measurements and values describe plants grown during the winter in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 3130'.

Parentage:

*Female, or seed, parent*.—Unnamed selection of *Helleborus niger*, not patented.

*Male, or pollen, parent*.—Unnamed selection of *Helleborus* x *hybridus*, not patented.

Propagation:

*Type*.—In vitro rhizome culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Sparse.

Plant description:

*Plant and growth habit*.—Herbaceous perennial; relatively compact, upright and mounding plant habit with flowers held above the foliar plane; plant shape, roughly flattened globular; moderately vigorous growth habit; moderate growth rate.

*Plant height, soil level to top of foliar plane*.—About 19.2 cm.

*Plant height, soil level to top of flowers*.—About 28.5 cm.

*Plant diameter* (*area of spread*).—About 45.4 cm.

Leaf description:

*Arrangement*.—Leaves arranged in a basal rosette; leaves palmately compound with typically seven leaflets per leaf.

*Leaf length*.—About 16.9 cm.

*Leaf width*.—About 18.3 cm.

*Leaflet length*.—About 10.5 cm.

*Leaflet width*.—About 4.9 cm.

*Leaf shape*.—Palmate; reniform in outline.

*Leaflet shape*.—Obovate to elliptic.

*Leaflet apex*.—Acute.

*Leaflet base*.—Attenuate.

*Leaflet margin*.—Serrate; lowest leaflets occasionally cleft.

*Leaflet texture and luster, upper surface*.—Smooth, glabrous; moderately leathery; moderately glossy.

*Leaflet texture and luster, lower surface*.—Smooth, glabrous; moderately leathery; slightly glossy.

*Leaflet venation pattern*.—Pinnate.

*Leaflet color*.—Developing leaflets, upper surface: Close to 137B. Developing leaflets, lower surface: Close to 146A to 146B. Fully developed leaflets, upper surface: Close to darker than between 147A and N189A; venation, close to 137B. Fully developed leaflets, lower surface: Close to 143B; venation, close to 144B.

*Petioles*.—Length: About 14.6 cm. Diameter: About 5 mm. Strength: Strong. Texture and luster, upper and lower surfaces: Smooth, glabrous; slightly glossy. Color, upper and lower surfaces: Close to 143A to 143B.

Flower description:

*Flower shape and habit*.—Single rotate flowers; arranged solitary or in small clusters with about three flowers each; freely flowering habit with about 45 flowers developing per plant; flowers facing outwardly to nodding.

*Fragrance*.—None detected.

*Natural flowering season*.—Plants begin flowering about ten months after planting; plants flower during the winter in Germany.

*Flower longevity on the plant*.—About ten days; sepals persistent, other flower parts not persistent.

*Flower buds*.—Length: About 2.4 cm. Diameter: About 1.5 cm. Shape: Ovoid. Texture and luster: Smooth, glabrous; matte. Color: Close to 145C to 145D heavily tinged with close to 182B and 183D.

*Inflorescence height*.—About 14.3 cm.

*Inflorescence diameter*.—About 12.6 cm.

*Flower diameter*.—About 7.7 cm.

*Flower depth* (*height*).—About 2.7 cm.

*Petals*.—Transformed into nectaries.

*Sepals*.—Quantity and arrangement: About five, arranged in a single whorl. Length: About 4.3 cm. Width: About 4.2 cm. Shape: Broadly ovate, slightly concave. Apex: Obtuse. Base: Cuneate. Margin: Entire; very slightly undulate. Texture and luster, upper and lower surfaces: Smooth, glabrous; matte. Color: When opening, upper surface: Close to between 69C to 69D and N155C; proximally, densely covered with spots, close to 187B and 187C. When opening, lower surface: Close to between 69B and 181D. Fully opened, upper surface: Close to NN155D; proximally, densely covered with spots, close to 187D. Fully opened, lower surface: Close to N155B; central blotch, close to 186D; venation, close to 63B.

*Flower bracts*.—Quantity per flower: Typically one. Length: About 5.8 cm. Width: About 5.8 cm. Shape: Palmate to trifoliate. Apex: Acute. Base: Broadly cuneate. Margin: Entire; distally, serrate; slightly undulate. Color, upper surface: Close to 137B. Color, lower surface: Close to 147B; main vein, close to 178A.

*Peduncles*.—Length: About 25.1 cm. Diameter: About 6 mm to 7 mm. Aspect: About 10° from vertical. Strength: Strong. Texture and luster: Smooth, glabrous; moderately glossy. Color: Close to 144A; densely covered and flushed with close to 182B.

*Pedicels*.—Length: About 2.2 cm. Diameter: About 3 mm. Aspect: About 25° from peduncle axis.

Strength: Moderately strong. Texture and luster: Smooth, glabrous; glossy. Color: Close to 197A.

*Reproductive organs*.—Stamens: Quantity per flower: About 120. Filament length: About 1.6 cm. Filament color: Close to 155B. Anther shape: Reniform; basifixed. Anther size: About 1.5 mm by 2 mm. Anther color: Close to 1C. Pollen amount: Scarce. Pollen color: Close to 4D. Pistils: Quantity per flower: About six. Pistil length: About 1.3 cm. Stigma diameter: About 0.3 mm. Stigma shape: Club-shaped. Stigma color: Close to 157A. Style length: About 1.25 cm. Style color: Close to 185C. Ovary color: Close to 146D. Nectaries (transformed petals): Quantity per flower: About 13 to 15. Length: About 1 cm. Diameter: About 3.5 mm. Shape: Tubular, flattened. Texture and luster, inner and outer surfaces: Smooth, glabrous; matte. Color, immature, inner and outer surfaces: Close to 143C. Color, mature, inner and outer surfaces: Close to N144B; towards the base, close to 152B to 152C; color becoming closer to 151A with subsequent development.

*Seeds and fruits*.—Seed and fruit development have not been observed on plants of the new *Helleborus* to date.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants to date.

It is claimed:

1. A new and distinct *Helleborus* plant named 'COSEH 3130' as illustrated and described.

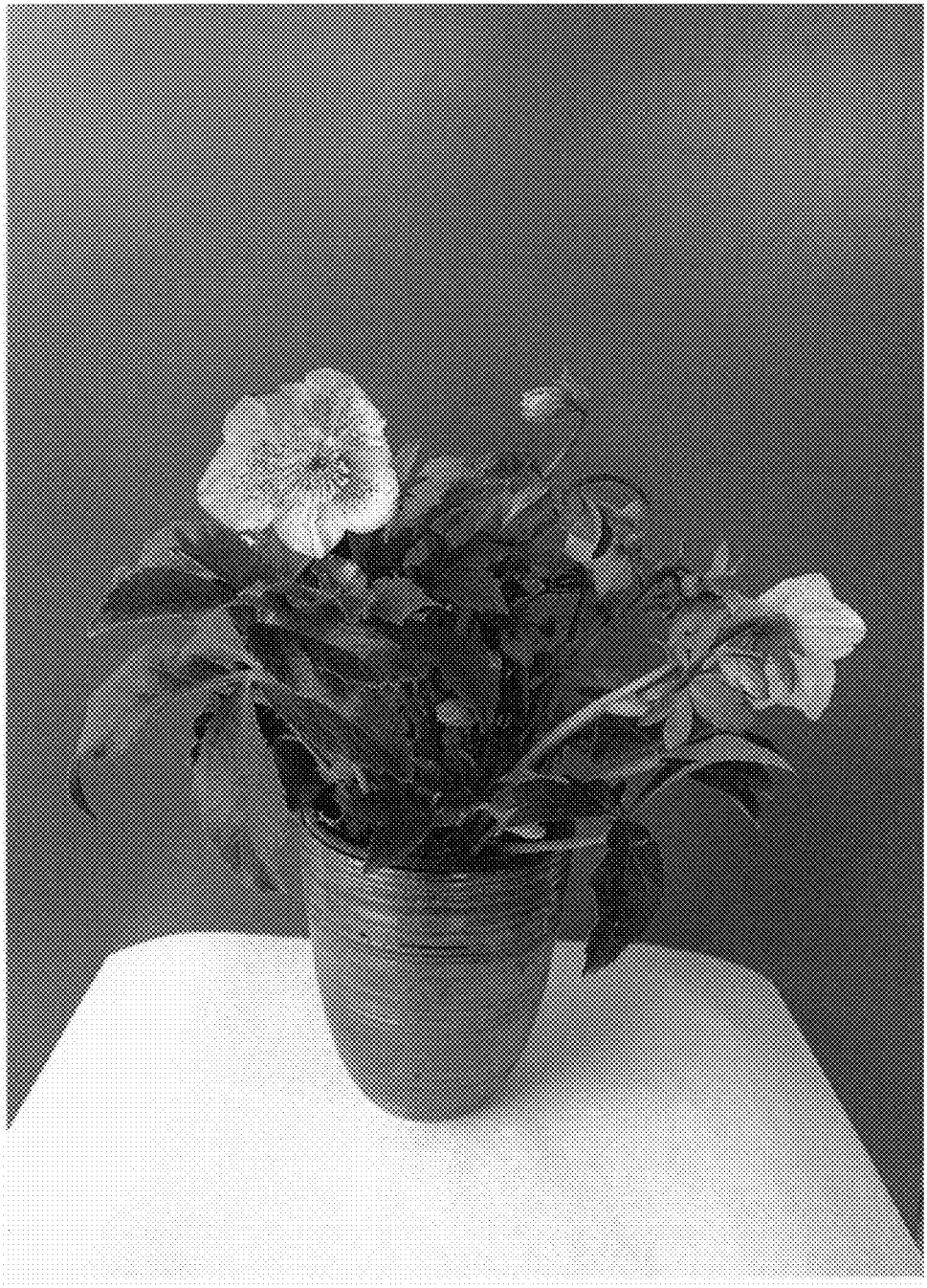

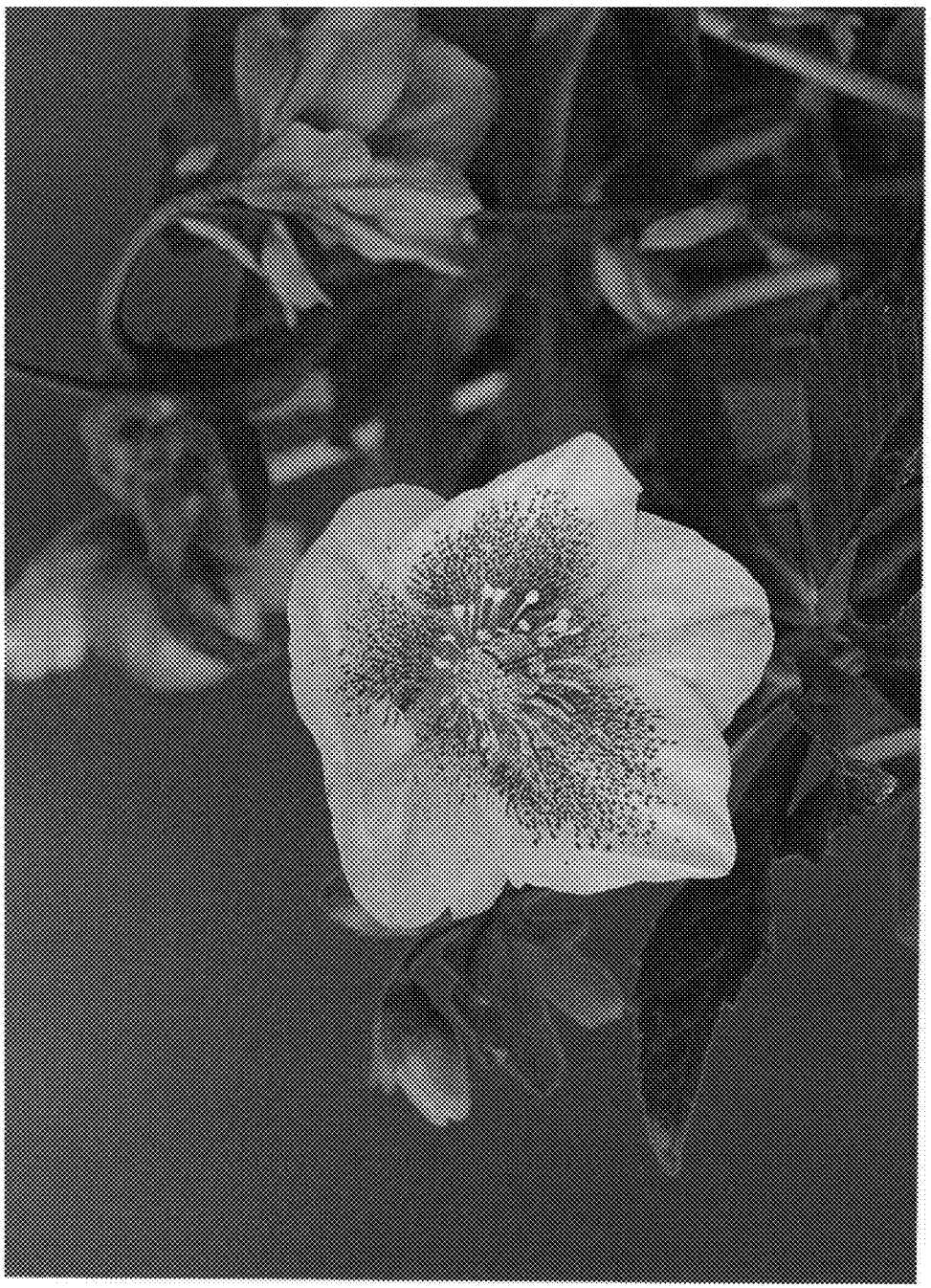

* * * * *